United States Patent [19]

Sanderson et al.

[11] Patent Number: 5,146,023

[45] Date of Patent: *Sep. 8, 1992

[54] PROCESS FOR OLIGOMERIZING OLEFINS TO PREPARE SYNTHETIC LUBRICANT BASE STOCKS HAVING IMPROVED PROPERTIES

[75] Inventors: John R. Sanderson, Leander; Edward T. Marquis, Austin, both of Tex.

[73] Assignee: Texaco Chemical Company, White Plains, N.Y.

[*] Notice: The portion of the term of this patent subsequent to Oct. 1, 2008 has been disclaimed.

[21] Appl. No.: 516,931

[22] Filed: Apr. 30, 1990

[51] Int. Cl.$^5$ ............................ C07C 2/74; C07C 2/02
[52] U.S. Cl. ...................................... 585/255; 585/10; 585/18; 585/522; 585/523; 585/533
[58] Field of Search ................ 585/10, 18, 255, 522, 585/523, 533

[56] References Cited

U.S. PATENT DOCUMENTS

| | | | |
|---|---|---|---|
| 1,919,722 | 7/1933 | Hyman | 585/533 |
| 2,543,016 | 2/1951 | Grasse | 585/255 |
| 2,574,895 | 1/1951 | Stecker | 585/533 |
| 2,951,087 | 8/1960 | Hauser et al. | 502/62 |
| 3,412,039 | 11/1968 | Miller | 252/428 |
| 3,432,571 | 3/1969 | Noddings et al. | 260/641 |
| 3,459,815 | 8/1969 | Noddings et al. | 260/641 |
| 3,845,150 | 10/1974 | Isoung-Yuan Yan et al. | 260/673.5 |
| 3,849,507 | 11/1990 | Zuech | 260/671 C |
| 4,153,638 | 5/1979 | Bercik et al. | 585/526 |
| 4,299,730 | 11/1981 | Sommer et al. | 252/435 |
| 4,329,257 | 5/1982 | Sommer et al. | 252/435 |
| 4,351,980 | 9/1982 | Reusser et al. | 585/820 |
| 4,380,509 | 4/1983 | Sommer et al. | 502/439 |
| 4,420,646 | 12/1983 | Darden et al. | 585/10 |
| 4,456,779 | 6/1984 | Owen et al. | 585/415 |
| 4,480,142 | 10/1984 | Cobb | 585/464 |
| 4,531,014 | 7/1985 | Gregory et al. | 585/415 |
| 4,604,491 | 8/1986 | Dressler et al. | 585/26 |
| 4,808,559 | 2/1989 | Sommer et al. | 502/63 |
| 4,827,064 | 5/1989 | Wu | 585/530 |
| 4,879,425 | 11/1989 | Kukes et al. | 585/350 |

FOREIGN PATENT DOCUMENTS 1489646 10/1977 United Kingdom .

OTHER PUBLICATIONS

Chauduri and Sharma, "Some Novel Aspects of the Dimerizative of Γ-methylstyrene with Acidic Ion-Exchange Resins, Clays, and other Acidic Materials as Catalysts," *Ind. Eng. Res.* vol. 28, pp. 1757-1763 (1989).

Purnell, "Catalysis by Ion-Exchanged Montmorillonites," *Catalysis Letters* 5(1990) pp. 203-210.

Kuliev et al., "Preparation of High-Viscosity Synthetic Lubricants Using an Aluminosilicate Catalyst," Institute of Petro Chemical Processes of the Academy of Sciences of the Agerbaidzhan SSR, Azerbaidzhanskor, Nestiano, Khoziastvo, 1983, No. 4, pp. 40-43.

Figueras, "Pillared Clays as Catalysts," *Catal. Rev.-Sci. Eng.*, 30(3) pp. 457-499 (1988).

Friedlander, "Organized Polymerization I. Olefins on a Clay Surface," *Journal of Polymer Science:* Part C, No. 4, pp. 1291-1301.

Friedlander et al., "Organized Polymerization III, Monomers Intercalted in Montmorillonite," *Polymer Letters,* vol. 2, pp. 475-479 (1964).

"Intercalated Catalysts and Pillared Clays," from a Process Evaluation Research Planning Report by Chem Systems, titled Catalysts:Selected Developments, 84-3, pp. 239-249 (Dec. 1985).

Bolan, "Synthetic Lubricant Base Stocks", Process Economics Program Report No. 125A by SRI International, Apr. 1989 and Supplement A, Sep. 1989.

"Synthetic Lubricants from Internal Olefins," Process Evaluation/Research Planning Report, Chem. Systems, 84-Q-1, pp. 17-45.

Adams, "Synthetic Organic Chemistry Using Pillared, Cation-Exchanged and Acid-Treated Montmoillonite Catalysts-A Review", *Applied Clay Science*, 2 (1987), pp. 309-342.

Adams et al., "Clays as Selective Catalysts in Organic Synthesis", *Journal of Inclusion Phenomena,* vol. 5 (1987), pp. 663-674.

Primary Examiner—Patrick P. Garvin
Assistant Examiner—E. D. Irzinski
Attorney, Agent, or Firm—Jack H. Park; Kenneth R. Priem; Russell R. Stolle

[57] ABSTRACT

A process is disclosed for preparing synthetic lubricant base stocks having improved properties. Synthetic lubricant base stocks may be prepared in good yield by oligomerizing linear olefins using certain acidic calcium montmorillonite clay catalysts. When a mixture of alpha and internal-olefins having up to 50 wt. % internal-olefin is used, and the oligomers prepared therefrom are hydrogenated, a synthetic lubricant base stock having a higher viscosity index and a lower pour point is prepared.

39 Claims, No Drawings

PROCESS FOR OLIGOMERIZING OLEFINS TO PREPARE SYNTHETIC LUBRICANT BASE STOCKS HAVING IMPROVED PROPERTIES

CROSS-REFERENCE TO RELATED APPLICATION

This application is related to co-pending U.S. Pat. application Ser. No. 07/500,631, filed Mar. 28, 1990, which relates to the preparation of synthetic lubricant base stocks by oligomerizing linear olefins by means of certain acidic montmorillonite clays.

BACKGROUND OF THE INVENTION

1. Field of the Invention

The invention relates to the preparation of synthetic lubricant base stocks, and more particularly to synthetic lubricant base stocks having improved properties, made by oligomerizing mixtures of internal and alpha-olefins by means of certain acidic montmorillonite clay catalysts.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher termperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a non-hazardous, non-polluting catalyst would be a substantial improvement in the art.

Kuliev et al. attempted to prepare synthetic lubricants by oligomerizing long-chain ($C_9$–$C_{14}$) olefins using non-hazardous and non-polluting acidic clays comprising sulfuric and hydrochloric acid-activated bentonites from the Azerbaidzhan SSR. See Kuliev, Abasova, Gasanova, Kotlyarevskaya, and Valiev, "Preparation of High-Viscosity Synthetic Lubricants Using an Aluminosilicate Catalyst," Institute of Petrochemical Processes of the Academy of Sciences of the Azerbaidzhan SSR, Azer. Neft. Khoz., 1983, No. 4, pages 40–43. However, Kuliev et al. concluded that "it was not possible to prepare viscous or high-viscosity oils by olefin polymerization over an aluminosilicate catalyst" and that "hydrogen redistribution reactions predominate with formation of aromatic hydrocarbon, coke, and paraffinic hydrocarbon." Gregory et al., on the other hand, used Wyoming bentonite to oligomerize shorter-chain olefins. (See U.S. Pat. No. 4,531,014.) However, like Kuliev et al., they also were unable to obtain a product high in dimer, trimer and tetramer, and low in disproportionation products.

Applicants discovered that it is possible to prepare synthetic lubricant base stocks in good yield by oligomerizing long-chain olefins using certain acidic montmorillonite clay catalysts. Applicants found that a high conversion of long-chain olefin to dimer, trimer, and tetramer may be obtained with formation of very little concomitant hydrogen redistribution by-product by using an acidic calcium montmorillonite clay having a moisture content ranging up to about 20 wt. %, a residual acidity in the range of about 3 to about 30 mg KOH/g (when titrated to a phenolphthalein end point), and a surface area of about 300 $M^2$/g or greater. In addition to being excellent catalysts, these clays are non-hazardous and non-polluting. With respect to the present invention, Applicants have discovered, surprisingly, that synthetic lubricant base stocks with an improved viscosity index and a lower pour point may be obtained where the oligomers are prepared by contacting a mixture of alpha and internal-olefins, comprising up to 50 wt. % internal-olefin, with the clay catalyst.

SUMMARY OF THE INVENTION

The invention relates to a process for the preparation of oligomers, comprising contacting a mixture of alpha and internal-olefins having at least 10 carbon atoms with a catalyst comprising an acidic calcium montmorillonite clay having a moisture content ranging up to about 20 wt. %, a residual acidity in the range of about 3 to about 30 mg KOH/g (when titrated to a phenolphthalein end point), and a surface area of about 300 $M^2/g$ or greater, in which the mixture of olefins is comprised of up to about 50 wt. % internal-olefin.

DESCRIPTION OF THE PREFERRED EMBODIMENTS

Synthetic lubricant base stocks may be prepared in good yield by oligomerizing long-chain olefins using certain acidic montmorillonite clay catalysts. Applicants have discovered that certain properties of these synthetic lubricant base stocks are improved when the olefin feed comprises a mixture of alpha and internal-olefin having up to about 50 wt. % internal-olefin. When oligomers produced in this manner are hydrogenated, they yield synthetic lubricant base stocks having higher viscosity indices. A higher viscosity index indicates that the synthetic lubricant will be less susceptible to a change in viscosity when subjected to a change in temperature. This is a desirable characteristic for most lubricating applications. Additionally, these synthetic lubricants have a lower pour point, another desirable feature.

The oligomerization reaction may be carried out in either a stirred slurry reactor or in a fixed bed continuous flow reactor. In a continuous reaction, up to about 50 wt. % of the olefin feed may be made to comprise internal-olefin by either or both of two methods. According to the first method, separate feedstreams of internal and alpha-olefins may be mixed in the desired weight-ratio prior to or upon entering the reactor containing the clay catalyst bed. Alternatively, or in addition, the second method provides that internal-olefin may be introduced to the catalyst bed in a recycle stream. When alpha-olefin in the feedstream passes through the clay catalyst in the reactor, a portion of the olefin remains un-oligomerized. Of the olefin remaining in monomer form, most will have isomerized to internal-olefin. Thus, the product of the oligomerization reaction has three components: oligomer; internal-olefin monomer; and alpha-olefin monomer. The alpha and internal-olefins may be stripped from the oligomer and recycled to the catalyst bed for oligomerization. The monomer stripping step should be conducted under mild conditions. Distillation at temperatures exceeding 210° C. may cause the oligomers to break down in some fashion and come off as volatiles. Preferably, therefore, the reboiler or pot temperature should be kept at or under about 80° C. when stripping out the monomer. Procedures known by those skilled in the art to be alternatives to fractional distillation also may be employed to separate the monomers from oligomers.

In summary, internal-olefin may be introduced to the catalyst bed directly as a feedstream component and/or as a recycled isomer of the alpha-olefin feed. Additionally, where internal-olefin is introduced as a feedstream component, any unoligomerized internal-olefin also may be recycled to the catalyst bed. When either or both methods are employed, no more than about 50 wt. % of the olefin present in the catalyst bed at any one time should comprise internal-olefin.

In a batch reaction system, internal-olefin should comprise up to about 50 wt. % of the olefin starting material. The internal-olefin component may be obtained by processes known to those skilled in the art, purchased commercially, and/or may be distilled from the product of a prior oligomerization reaction and recycled by inclusion in a subsequent batch oligomerization reaction.

The alpha-olefin feedstocks used in the present invention may be selected from compounds having the formula $R''CH=CH_2$, where $R''$ is an alkyl radical of 8 to 22 carbon atoms. The internal-olefins used as feedstocks in the present invention and/or comprising recycled by-product should have the formula $RCH=CHR'$, where R and R' are the same or different alkyl radicals of 1 to 20 carbon atoms, provided that the total number of carbon atoms in any internal or alpha-olefin shall be within the range of 10 to 24, inclusive. A preferred range for the total number of carbon atoms in any internal or alpha-olefin molecule is 12 to 18, inclusive, with an especially preferred range being 13 to 16, inclusive. Mixtures of olefins having different numbers of carbon atoms may be used, provided that the total number of carbon atoms in any one olefin shall be within the range of 10 to 24, inclusive. Alpha and internal-olefin feedstocks may be obtained by processes well-known to those skilled in the art and are commercially available.

The oligomerization reaction may be represented by the following general equation:

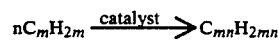

where n represents moles of monomer and m represents the number of carbon atoms in the monomer. Thus, the oligomerization of decene, with the double bond in an alpha or internal position, may be represented as follows:

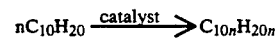

The reaction occurs sequentially. Initially, olefin monomer reacts with olefin monomer to form dimers. The dimers that are formed then react with additional olefin monomer to form trimers, and so on. This results in an oligomer product distribution that varies with reaction time. As the reaction time increases, the olefin monomer conversion increases, and the selectivities for the heavier oligomers increase. Generally, each resulting oligomer contains one double bond.

The catalysts used to effect this reaction in the present invention are certain silica-alumina clays, also called aluminosilicates. Silica-alumina clays primarily are composed of silicon, aluminum, and oxygen, with minor amounts of magnesium and iron in some cases. Variations in the ratios of these constituents, and in their crystal lattice configurations, result in some fifty separate clays, each with its own characteristic properties.

One class of silica-alumina clays comprises smectite clays. Smectite clays have a small particle size and unusual intercalation properties which afford them a high surface area. Smectites comprise layered sheets of octahedral sites between sheets of tetrahedral sites, where the distance between the layers can be adjusted by swelling, using an appropriate solvent. Three-layered sheet-type smectites include montmorillonites. The montmorillonite structure may be represented by the following formula:

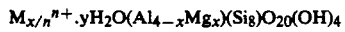

where M represents the interlamellar (balancing) cations, normally sodium or lithium; and x, y and n are integers.

Montmorillonite clays may be acid-activated by such mineral acids as sulfuric acid and hydrochloric acid. Mineral acids activate montmorillonites by attacking and solubilizing structural cations in the octahedral layers. This opens up the clay structure and increases surface area. These acid-treated clays act as strong Bronsted acids. Applicants discovered that certain acid-treated montmorillonite clay catalysts are particularly effective for preparing synthetic lubricant base stocks in good yield by oligomerizing long-chain olefins. These clays are acidic calcium montmorillonite clays having a moisture content ranging up to about 20 wt. %, a residual acidity in the range of about 3 to about 30 mg KOH/g (when titrated to a phenolphthalein end point), and a surface area of about 300 $M^2/g$ or greater. Illustrative examples include Filtrol grade 24, having a moisture content of 12 wt. %, a residual acidity of 8.5 mg KOH/g, and a surface area of 425 $M^2/g$; Filtrol grade 124, having a moisture content of 2 wt. %, a residual acidity of 7.0 mg KOH/g, and a surface area of 400 $M^2/g$; Filtrol grade 13, having a moisture content of 16 wt. %, a residual acidity of 15 mg KOH/g, and a surface area of 300 $M^2/g$; Filtrol grade 113, having a moisture content of 4 wt. %, a residual acidity of 10 mg KOH/g, and a surface area of 300 $M^2/g$; and Filtrol grade 224, having virtually no moisture, and having a residual acidity of 3.0 mg KOH/g, and a surface area of 350 $M^2/g$.

Preferably, the catalyst is activated by heat treatment before running the reaction. Applicants found, surprisingly, that heat treatment of the catalyst prior to running the oligomerization reaction causes the catalyst to be more active and produce a higher olefin conversion. Additionally, clays heat treated in this manner are more stable, remaining active during the oligomerization reaction for a longer period of time. The clays may be heat treated at temperatures in the range of about 50° to 400° C., with or without the use of a vacuum. A more preferred temperature range is 50° to 300° C. Optionally, an inert gas may be used during heat treatment as well. Preferably, the clay should be heat treated under conditions and for a length of time which will reduce the water content of the clay to approximately 1 wt. % or less. The catalyst concentration should be sufficient to provide the desired catalytic effect. The temperatures at which the oligomerization may be performed are between about 50° and 300° C., with the preferred range being about 150° to 180° C. The reaction may be run at pressures of from 0 to 1000 psig.

Following the oligomerization reaction, the unsaturated oligomers may be hydrogenated to improve their thermal stability and to guard against oxidative degradation during their use as lubricants. The hydrogenation reaction for decene oligomers may be represented as follows:

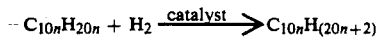

where n represents moles of monomer used to form the oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

If in a continuous reaction the recycle stream is not employed, it is desirable to strip any un-oligomerized monomer from the oligomer product. However, while it is known to further distill the oligomer product to obtain products of various 100° C. viscosities, it is preferred in the method of the present invention that no further distillation (i.e. beyond the monomer flashing) be conducted. In other words, the monomer-stripped, hydrogenated bottoms are the desired synthetic lubricant components. Batch reaction products also require no additional distillation beyond removal of any remaining monomer. Thus, the method of this invention, with or without the recycle stream, does not require the costly, customary distillation step following hydrogenation, yet, surprisingly, produces a synthetic lubricant component that has excellent properties and that performs in a superior fashion. However, in some contexts, one skilled in the art may find subsequent distillation useful in the practice of this invention. The monomer stripping step should be conducted under mild conditions, as discussed in connection with the recycle stream.

The invention will be further illustrated by the following examples, which are given by way of illustration and not as limitations on the scope of this invention.

EXAMPLES

In the examples offered to illustrate the present invention, the following procedures were used:

Batch-Flask

Olefin and clay catalyst were charged to a flask equipped with a stirrer, thermometer, heating mantle, and a water-cooled condenser ($N_2$ purge). The mixture was vigorously stirred and heated to a desired temperature for the desired time. The mixture was then cooled to ambient temperature and filtered with suction. The liquid was analyzed by liquid chromatography. The results are detailed in Tables I and III.

Batch-Autoclave

Olefin and clay catalyst were charged to an autoclave. The autoclave was sealed and heated to the desired temperature for the desired time. The mixture was then cooled to ambient temperature and filtered with suction. The liquid was then analyzed by liquid chromatography. The results are shown in Tables I and III.

Hydrogenation of Oligomer

An autoclave was charged with oligomer and finely powdered nickel catalyst. The autoclave was flushed with hydrogen and then pressured to 1000 psig with hydrogen. The mixture was heated to 200° C. and stirred at this temperature for 4 hours. The mixture was then repressured with hydrogen to 2000 psig as needed. The mixture was then cooled to ambient temperature, the catalyst was filtered and the monomer was removed. The results are shown in Tables II and IV.

TABLE I
ACID CLAY CATALYZED OLEFIN OLIGOMERIZATION WITH INTERNAL/ALPHA-OLEFIN MIXTURES

| EXAMPLE NO. | OLEFIN | (g) | HARSHAW/FILTROL CATALYST | (g) | REACTOR | TIME (HR.) | TEMP. (°C.) | CON. (%) | M (%) | D (%) | T+ (%) | D/T+ RATIO |
|---|---|---|---|---|---|---|---|---|---|---|---|---|
| 1 | C-14A, 16A (63%, 36%) | 400 | H/F Clay 113 | 40 | Clave | 4 | 180° | 84.8 | 15.2 | 49.9 | 34.9 | 1.43 |
| 2 | C-14A, 16A C-16I | 200 200 | H/F Clay-24 | 40 | Flask | 6 | 150 | 71.1 | 28.9 | 48.1 | 23.0 | 2.09 |
| 3 | C-14A, 16A C-16I | 200 200 | H/F Clay-24 | 40 | Clave | 4 | 180 | 80.1 | 19.9 | 50.8 | 29.3 | 1.73 |
| 4 | C-14A, 16A C-16I | 300 100 | H/F Clay-24 | 40 | Clave | 4 | 180 | 78.2 | 21.8 | 52.5 | 25.8 | 2.03 |

Con. = Conversion; M = Monomer; D = Dimer; T+ = Trimer, plus Tetramer, Pentamer, etc.
A = Alpha; I = Internal

TABLE II
PROPERTIES OF REDUCED OLIGOMER BOTTOMS

| EXAMPLE NO. | Percent Remaining by TGA at 250° F. | Viscosity at 210° F. | VI | Pour Point (°F.) |
|---|---|---|---|---|
| 1 | 89.5 | 6.17 | 131 | −20 |
| 2 | 87.8 | 5.21 | 135 | −25 |
| 3 | 92.5 | 5.79 | 129 | −35 |
| 4 | 87.5 | 5.68 | 130 | −35 |

TGA = Thermogravimetric Analysis
VI = Viscosity Index

TABLE III
ACID CLAY CATALYZED OLEFIN OLIGOMERIZATIONS USING RECYCLE OLEFIN

| EXAMPLE NO. | OLEFIN | (g) | CATALYST | (g) | REACTOR | TIME (Hr.) | TEMP. (°C.) | Con. (%) | M (%) | D (%) | T+ (%) | D/T+ Ratio |
|---|---|---|---|---|---|---|---|---|---|---|---|---|
| 5 | 14A | 400 | H/F Clay-124 | 40 | Clave | 5 | 160 | 78.3 | 21.7 | 48.8 | 29.5 | 1.65 |
| 6 | 14A 14-recycle | 300 100 | H/F Clay-124 | 40 | Clave | 5 | 160 | 74.6 | 25.4 | 47.2 | 27.5 | 1.72 |
| 7 | 14A 14-recycle | 300 100 | H/F Clay-124 | 40 | Flask | 5 | 160 | 74.7 | 25.3 | 48.5 | 26.2 | 1.85 |
| 8 | 14A 14-recycle | 300 100 | H/F Clay-124 | 40 | Flask | 5 | 160 | 74.9 | 25.1 | 45.2 | 29.7 | 1.52 |

TABLE IV
PROPERTIES OF REDUCED OLIGOMER BOTTOMS

| EXAMPLE NO. | Wt. % Recycle | Percent Remaining by TGA at 250° F. | Viscosity at 210° F. (cSt) | VI | Pour Point (°F.) |
|---|---|---|---|---|---|
| 5 | 0 | 88.5 | 6.61 | 121 | −20 |
| 6 | 25 | 85.9 | 5.14 | 127 | −30 |
| 7 | 25 | 83.0 | 5.09 | 127 | −35 |
| 8 | 25 | 80.5 | 4.99 | 126 | −35 |

We claim:

1. A process for the preparation of oligomers, comprising contacting a mixture of alpha and internal-olefins having from 10 to 24 carbon atoms with a catalytically effective amount of an acidic calcium montmorillonite clay having a moisture content ranging up to about 20 wt. %, a residual acidity in the range of about 3 to about 30 mg KOH/g, and a surface area of about 300 M$^2$/g or greater, and in which the mixture of olefins is comprised of up to about 50 wt. % internal-olefin.

2. The process of claim 1, wherein the olefins contain from 12 to 18 carbon atoms.

3. The process of claim 1, wherein the olefins contain from 12 to 18 carbon atoms and wherein the clay, before being contacted with the olefins, is heat treated to a moisture content of about 1 wt. % or less.

4. The process of claim 1, wherein the mixture of olefins is comprised of between about 5 to about 50 wt. % internalolefin.

5. The process of claim 1, wherein the moisture content of the clay is about 12 wt. %, the residual acidity is about 8.5 mg KOH/g, and the surface area is about 425 M$^2$/g.

6. The process of claim 1, wherein the moisture content of the clay is about 2 wt. %, the residual acidity is about 7.0 mg KOH/g, and the surface area is about 400 M$^2$/g.

7. The process of claim 1, wherein the moisture content of the clay is about 16 wt. %, the residual acidity is about 15 mg KOH/g, and the surface area is about 300 M$^2$/g.

8. The process of claim 1, wherein the moisture content of the clay is about 4 wt. %, the residual acidity is about 10 mg KOH/g, and the surface area is about 300 M$^2$/g.

9. The process of claim 1, wherein the moisture content of the clay is essentially nil, the residual acidity is about 3.0 mg KOH/g, and the surface area is about 350 M$^2$/g.

10. The process of claim 1, wherein the olefin mixture is contacted with the clay at a temperature of about 150° to about 180° C.

11. A process for the preparation of oligomers, comprising contacting a mixture of alpha and internal-olefins having from 12 to 18 carbon atoms with a catalytically effective amount of an acidic montmorillonite clay having a moisture content ranging up to about 20 wt. %, a residual acidity in the range of about 3 to about 30 mg KOH/g, and a surface area of about 300 M$^2$/g or greater, and in which the mixture of olefins is comprised of up to about 50 wt. % internal-olefin.

12. The process of claim 11, wherein the mixture of olefins is comprised of between about 5 to about 50 wt. % internal-olefin.

13. The process of claim 11, wherein the moisture content of the clay is about 12 wt. %, the residual acidity is about 8.5 mg KOH/g, and the surface area is about 425 $M^2/g$.

14. The process of claim 11, wherein the moisture content of the clay is about 2 wt. %, the residual acidity is about 7.0 mg KOH/g, and the surface area is about 400 $M^2/g$.

15. The process of claim 11, wherein the moisture content of the clay is about 16 wt. %, the residual acidity is about 15 mg KOH/g, and the surface area is about 300 $M^2/g$.

16. The process of claim 11, wherein the moisture content of the clay is about 4 wt. %, the residual acidity is about 10 mg KOH/g, and the surface area is about 300 $M^2/g$.

17. The process of claim 11, wherein the moisture content of the clay is essentially nil, the residual acidity is about 3.0 mg KOH/g, and the surface area is about 350 $M^2/g$.

18. The process of claim 11, wherein the olefin mixture is contacted with the clay at a temperature of about 150° to about 180° C.

19. The process of claim 11, wherein the clay, before being contacted with the olefins, is heat treated to a moisture content of about 1 wt. % or less.

20. A process for the preparation of oligomers, comprising the following steps:
   (a) contacting an alpha-olefin containing from 10 to 24 carbon atoms with a catalytically effective amount of an acidic calcium montmorillonite clay having a moisture content ranging up to about 20 wt. %, a residual acidity in the range of about 3 to about 30 mg KOH/g, and a surface area of about 300 $M^2/g$ or greater;
   (b) distilling the product of step (a) to separate the oligomers prepared in step (a) from a monomer fraction at least partially comprising internal olefin;
   (c) recycling the monomer fraction of step (b) to mix said fraction with the alpha-olefin feed of step (a) in a ratio such that the internal-olefin from the recycled monomer fraction comprises up to 50 wt. % of the mixture; and
   (d) contacting the mixture of step (c) with the clay of step (a).

21. The process of claim 20, wherein the olefins contain from 12 to 18 carbon atoms.

22. The process of claim 20, wherein the olefins contain from 12 to 18 carbon atoms and wherein the clay, before being contacted with the olefins, is heat treated to a moisture content of about 1 wt. % or less.

23. The process of claim 20, wherein the monomer fraction in step (c) is mixed with the alpha-olefin feed of step (a) in a ratio such that the internal-olefin from the recycled monomer fraction comprises about 5 to about 50 wt. % of the mixture.

24. The process of claim 20, wherein the moisture content of the clay is about 12 wt. %, the residual acidity is about 8.5 mg KOH/g, and the surface area is about 425 $M^2/g$.

25. The process of claim 20, wherein the moisture content of the clay is about 2 wt. %, the residual acidity is about 7.0 mg KOH/g, and the surface area is about 400 $M^2/g$.

26. The process of claim 20, wherein the moisture content of the clay is about 16 wt. %, the residual acidity is about 15 mg KOH/g, and the surface area is about 300 $M^2/g$.

27. The process of claim 20, wherein the moisture content of the clay is about 4 wt. %, the residual acidity is about 10 mg KOH/g, and the surface area is about 300 $M^2/g$.

28. The process of claim 20, wherein the moisture content of the clay is essentially nil, the residual acidity is about 3.0 mg KOH/g, and the surface area is about 350 $M^2/g$.

29. The process of claim 20, wherein the olefin mixture is contacted with the clay at a temperature of about 150° to about 180° C.

30. A process for the preparation of oligomers, comprising the following steps:
   (a) contacting a mixture of alpha and internal-olefins containing from 10 to 24 carbon atoms with a catalytically effective amount of an acidic calcium montmorillonite clay having a moisture content ranging up to about 20 wt. %, a residual acidity in the range of about 3 to about 30 mg KOH/g, and a surface area of about 300 $M^2/g$ or greater, and in which the mixture of olefins is comprised of up to about 50 wt. % internal-olefin;
   (b) distilling the product of step (a) to separate the oligomers prepared in step (a) from a monomer fraction at least partially comprising internal-olefin;
   (c) recycling the monomer fraction of step (b) to mix said fraction with the alpha and internal-olefin mixture of step (a) in a ratio such that the total internal-olefin present in the mixture comprises up to about 50 wt. % of the mixture; and
   (d) contacting the mixture resulting from step (c) with the clay in step (a).

31. The process of claim 30, wherein the olefins contain from 12 to 18 carbon atoms.

32. The process of claim 30, wherein the olefins contain from 12 to 18 carbon atoms and wherein the clay, before being contacted with the olefins, is heat treated to a moisture content of about 1 wt. % or less.

33. The process of claim 30, wherein the monomer fraction of step (b) is mixed with the alpha and internal-olefin mixture of step (a) in a ratio such that the total internal-olefin present in the mixture comprises about 5 to about 50 wt. % of the mixture.

34. The process of claim 30, wherein the moisture content of the clay is about 12 wt. %, the residual acidity is about 8.5 mg KOH/g, and the surface area is about 425 $M^2/g$.

35. The process of claim 30, wherein the moisture content of the clay is about 2 wt. %, the residual acidity is about 7.0 mg KOH/g, and the surface area is about 400 $M^2/g$.

36. The process of claim 30, wherein the moisture content of the clay is about 16 wt. %, the residual acidity is about 15 mg KOH/g, and the surface area is about 300 $M^2/g$.

37. The process of claim 30, wherein the moisture content of the clay is about 4 wt. %, the residual acidity is about 10 mg KOH/g, and the surface area is about 300 $M^2/g$.

38. The process of claim 30, wherein the moisture content of the clay is essentially nil, the residual acidity is about 3.0 mg KOH/g, and the surface area is about 350 $M^2/g$.

39. The process of claim 30, wherein the olefin mixture is contacted with the clay at a temperature of about 150° to about 180° C.

* * * * *